US00RE37148E

(19) United States
(12) Reissued Patent
Shank

(10) Patent Number: US RE37,148 E
(45) Date of Reissued Patent: Apr. 24, 2001

(54) GUIDEWIRE TIP CONSTRUCTION

(75) Inventor: Peter J. Shank, Burlington, MA (US)

(73) Assignee: Medtronic AVE, Inc., Santa Rosa, CA (US)

(21) Appl. No.: 08/654,630

(22) Filed: May 29, 1996

Related U.S. Patent Documents

Reissue of:
(64) Patent No.: 5,365,942
Issued: Nov. 22, 1994
Appl. No.: 07/904,436
Filed: Jun. 25, 1992

U.S. Applications:

(63) Continuation-in-part of application No. 07/620,796, filed on Dec. 3, 1990, now abandoned, which is a continuation of application No. 07/532,381, filed on Jun. 4, 1990, now Pat. No. 5,147,317.

(51) Int. Cl.[7] ..... A61M 5/00
(52) U.S. Cl. ..... 604/264
(58) Field of Search ..... 604/170, 164–169, 604/158; 600/585, 434

(56) References Cited

U.S. PATENT DOCUMENTS 3,452,742 7/1969 Muller .
4,748,986 6/1988 Morrison et al. .
4,811,743 3/1989 Stevens .
4,832,047 * 5/1989 Sepetka et al. ..... 128/772
4,846,186 7/1989 Box et al. .

OTHER PUBLICATIONS

ACS Product Bulletin dated Mar. 1990 describing Hi–Torque Floppy 0.010" guidewire with a tapering core.
ACS Product Bulletin dated Jun. 1990 describing Hi–Torque 0.010" guidewire having a tapering core and a flattened distal tip.
ACS 0.10 HTF Guidewire Drawings.
Cordius Super Soft "B" Guidewire Drawings.
ASC HTFII Guidewire Drawings.

* cited by examiner

*Primary Examiner*—Manuel Mendez
(74) *Attorney, Agent, or Firm*—Sterne, Kessler, Goldstein & Fox P.L.L.C.

(57) ABSTRACT

A guidewire for use in guiding a catheter has a tip construction that includes a core wire within a helical coil. The core wire has a distal tip segment that is tapered and is further impressed with a pair of opposed flattened surfaces extending along the taper, the surfaces lying at an angle to each other and defining a progressively flattened tip having increased width in a distal direction to define a duck-bill configuration. The tip construction provides improved column strength at the tip to resist guidewire prolapse while providing excellent torsional and flexibility characteristics.

38 Claims, 4 Drawing Sheets

GUIDEWIRE TIP CONSTRUCTION

Matter enclosed in heavy brackets [ ] appears in the original patent but forms no part of this reissue specification; matter printed in italics indicates the additions made by reissue.

RELATED APPLICATION

This application is a continuation-in-part of U.S. patent application Ser. No. 07/620,796 filed on Dec. 3, 1990, now abandoned, which is a continuation of U.S. patent application Ser. No. 07/532,381, U.S. Pat. No. 5,147,317 filed Jun. 4, 1990 and entitled LOW FRICTION VARIED RADIOPACITY GUIDEWIRE FOR USE WITH CATHETERS.

FIELD OF THE INVENTION

This invention relates to guidewires used to assist in the placement of catheters in body lumens and, particularly, to an improved tip structure for such guidewires.

BACKGROUND OF THE INVENTION

Guidewires are used in numerous catheterization procedures as an aid to placement of a catheter at a selected site within the human body. The catheter is constructed to perform a particular procedure at that internal site. Among the more common uses of guidewires is in the catheterization of blood vessels for diagnostic or therapeutic purposes. In a common type of vascular catheterization procedure, the guidewire first is inserted, usually percutaneously, into one of the patient's blood vessels and is manipulated and advanced through the branches of the vascular system to the target site. The catheter then is threaded over and advanced along the guidewire, with the guidewire serving to guide the catheter directly to the target site.

By way of further example, a number of catheterization procedures are performed with respect to the coronary arteries. In one such procedure for diagnostic purposes, an angiographic catheter is advanced through the patient's arteries to the entrance to the coronary arteries. A radiopaque contrast liquid then is injected through the angiographic catheter into the coronary arteries under X-ray fluoroscopy, so that the anatomy of the patient's coronary arteries may be observed visually. Once the coronary anatomy has been determined, the physician may perform additional catheterization procedures, including percutaneous transluminal coronary angioplasty (PTCA), in which a balloon catheter or other angioplasty catheter is advanced into the coronary arteries to widen an obstructed portion (stenosis) of the artery.

In a typical PTCA procedure, an angioplasty catheter, which may be in the form of an elongate flexible shaft with an inflatable balloon at its distal end, is advanced from the percutaneous puncture site in the patient's femoral artery through the patient's arteries toward the heart and into the coronary arteries. The catheter is guided to the target site of the obstruction by use of a slender guidewire which initially is advanced into and manipulated through the coronary arteries in advance of the dilatation catheter. Once the distal end of the guidewire is in place within the obstruction, the catheter then is advanced over the guidewire which guides the catheter directly to the obstruction to place its balloon within the obstruction. The balloon then is inflated to dilate the obstructed portion of the artery, thereby enlarging the flow area through the artery.

Guidewires used with PTCA catheters are of special design. Although they are extremely slender, of the order of 0.010 to 0.018 inches in diameter, they nevertheless must be capable of transmitting rotation from the proximal end of the guidewire to the distal end in order that the physician may controllably steer the guidewire through the branches of the patient's arteries and manipulate it to the target site in the intended coronary artery. Additionally, the distal end of the guidewire must be sufficiently flexible in order that the distal portion of the guidewire can pass through sharply curved tortuous coronary anatomy as well as to provide a sufficiently soft, distal tip that will not injure the artery or its delicate inner lining. It also is among the desirable features of a guidewire that it have sufficient column strength so that it can be pushed without buckling.

Among the common guidewire configurations used in angioplasty is the type of guidewire illustrated in U.S. Pat. No. 4,545,390 (Leary). Such a wire includes an elongate flexible shaft, typically formed from stainless steel, having a tapered distal portion and a helical coil mounted to and about the tapered distal portion. The generally tapering distal portion of the shaft acts as a core for the coil and results in a guidewire having a distal portion of increasing flexibility that is adapted to follow the contours of the vascular anatomy while still being capable of transmitting rotation from the proximal end of the guidewire to the distal end so that the physician can controllably steer the guidewire through the patient's blood vessels. The characteristics of the guidewire are affected significantly by the details of construction as the distal tip of the guidewire. For example, in one type of tip construction, the tapering core wire extends fully through the helical coil to the distal tip of the coil and is attached directly to a smoothly rounded tip weld at the distal tip of the coil. Such a construction typically results in a relatively stiff tip suited particularly for use when attempting to push the guidewire through a tight stenosis. In addition to a high degree of column strength, such a tip also displays excellent torsional characteristics.

In another type of tip construction, the tapered core wire terminates short of the tip weld. It is common in such a construction to attach a very thin metallic ribbon at one (proximal) end to the core wire and at its other (distal) end to the tip weld. The ribbon serves as a safety element to maintain the connection between the core wire and the distal tip weld in the event of coil breakage. It also serves to retain a bend formed in the ribbon to maintain the tip in a bent configuration as is desirable when manipulating and steering the guidewire. Additionally, by terminating the core wire short of the tip weld, the segment of the helical coil between the distal end of the core wire and the tip weld is very flexible and floppy. The floppy tip is desirable in situations where the vasculature is highly tortuous and in which the guidewire must be capable of conforming to and following the tortuous anatomy with minimal trauma to the blood vessel.

In another type of tip construction, the distal-most segment of the core wire is hammered flat (flat-dropped) so as to serve the same function as the shaping ribbon but as an integral unitary piece with the core wire. The tip of the flat dropped segment is attached to the tip weld.

Although each of the above-described tip constructions has its advantages, each also presents some compromises and difficulties. Although the construction in which the core extends fully to and is attached to the tip weld is suited particularly for crossing a very tight stenosis, it may be unsuitable in those instances where a more tortuous anatomy with a less restrictive stenosis is encountered. Among the difficulties presented with the floppy type of tip construction is that the relatively poor column strength of the distal tip sometimes causes the floppy tip to prolapse, that is, to buckle and fold back on itself. For example, when the guidewire is negotiating tortuous anatomy, the physician may have been successful in maneuvering a portion of the guidewire tip partially into a particularbranch artery. With the very floppy distal tip, however, it sometimes occurs that when the physician pushes on the guidewire, the relatively poor column strength of the distal tip causes it to prolapse so that the trailing, stiffer portion of the guidewire does not follow into that branch but, instead, tends to advance straight ahead. That, in turn, pulls the portion of the tip that had entered the branch artery out of the branch artery. That may result in prolapse of the wire and, in the worst case, the formation of a permanent kink in the tip of the guidewire which destroys the steerability of the guidewire, thus rendering it unsuitable for further use. Consequently, it may become necessary to remove the guidewire, reshape it or replace it with an undamaged guidewire.

It would be desirable, therefore, to provide a tip construction for a guidewire which is sufficiently floppy so as to be atraumatic and follow the contour of tortuous anatomy, which displays good torque transmission to facilitate steering yet also provides improved column strength to reduce the risk of prolapse of the distal tip of the guidewire. It is among the general objects of the invention to provide such an improved guidewire tip construction.

SUMMARY OF THE INVENTION

In accordance with the invention, an improved tip construction for a guidewire is provided in which the reduced diameter distal portion of the core wire includes a distalmost segment that is tapered and is flattened to define a pair of wedge-like surfaces which appear, in plan, to form a "duck-bill" shape. The tip of the flattened portion is attached directly to the tip weld at the distal end of the coil. By flattening the distal tip segment in a wedge-like, duck-bill shape configuration, the steerability, torque responsiveness and column strength of the tip is improved without materially adversely affecting the floppiness of the tip configuration. The overall performance of the guidewire then is improved significantly.

It is among the general objects of the invention to provide an improved tip construction for a guidewire.

Another object of the invention is to provide an improved tip construction for a guidewire which displays an improved combination of torque responsiveness, floppiness and column strength.

Another object of the invention is to provide improved tip construction for a guidewire in which the distal tip segment of the core wire is flattened in a wedge, duck-bill shape.

Another object of the invention is to provide a tip construction for a guidewire in which a tapered tip segment is provided with flattened surfaces.

Another object of the invention is to provide a tip construction for a guidewire in which a tapered tip segment is provided with flattened surfaces without sharp transitions between the flattened and unflattened surfaces.

A further object of the invention is to provide an improved tip construction for a guidewire in which a tapered tip segment is provided with a flattened tip that defines wedge-like surfaces that are of progressively increasing width in a distal direction.

Another object of the invention is to provide an improved tip construction for a guidewire in which a core wire extending through a helical coil is provided with a broad flat tip that spans the major portion of the inner diameter of the helical coil.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
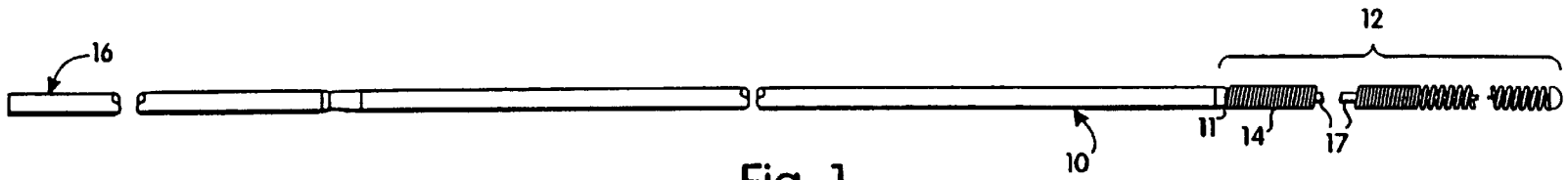
FIG. 1 is a fragmented overall illustration of a guidewire of a type that may incorporate the invention.

FIG. 1 illustrates one type of guidewire that may incorporate the invention. The guidewire includes an elongate flexible shaft 10 formed from an appropriate material, such as stainless steel. The guidewire may be considered as having a proximal end (to the left in FIG. 1) and a distal end (to the right in FIG. 1). The distal end is intended to be inserted into the patient with the proximal end remaining out of the patient so that it can be manipulated by the physician. A distal portion 12 of the shaft 10 is tapered. An elongate flexible helical coil 14 is attached to and extends about the distal portion of the shaft 10. The coil preferably is attached at its proximal end to the shaft 10 at a proximal braze joint 11. The coil also may be attached to the distal portion 12 of the shaft 10 at a distal braze joint 13. The coil 14 preferably is formed from a suitable highly radiopaque alloy such as a gold-platinum or a platinum-tungsten alloy. The coil may be formed from wire of the order of 0.002 inches to 0.003 inches in diameter. By way of further example, the guidewire may incorporate structure disclosed generally in U.S. Pat. No. 4,545,390 (Leary), the disclosure of which is hereby incorporated by reference herein in its entirety. The tapered distal portion may be tapered continuously or in a step tapered configuration, for example, as disclosed in U.S. Pat. No. 4,922,924 issued May 8, 1990, the disclosure of which is hereby incorporated by reference in its entirety. The proximal end of the shaft may be provided with a tubular socket 16 for connection with a guidewire extension as described in U.S. Pat. No. 4,917,103 (Gambale) and U.S. patent application Ser. No. 206,008 filed Jun. 13, 1988 (Palermo), the disclosures of which are hereby incorporated herein in their entireties.

Figure 2:
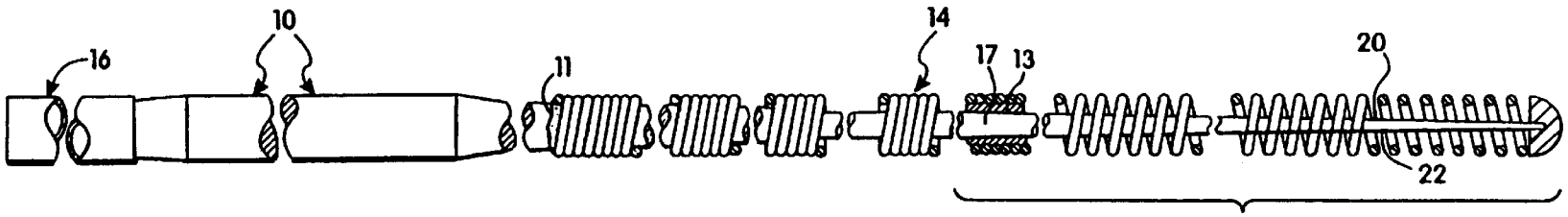
FIG. 2 is a more enlarged, fragmented, cross-sectional illustration of the guidewire in accordance with the invention showing the distal region in greater detail.
Figure 4:
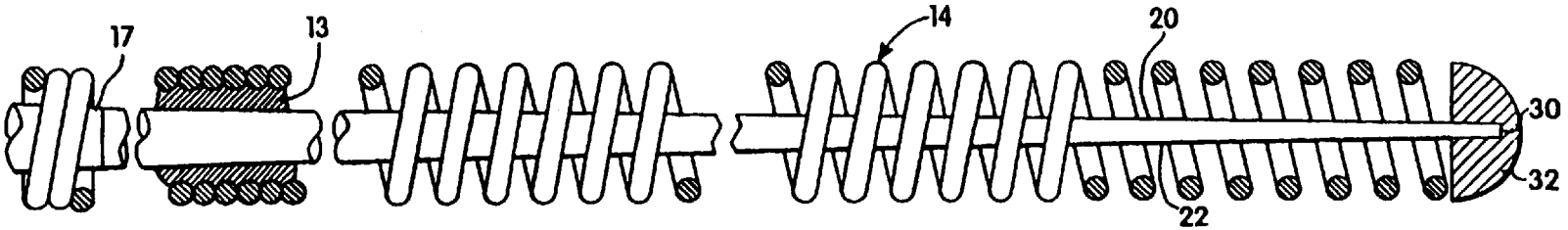
FIG. 4 is an illustration similar to FIG. 3 showing the tip of the core wire in side elevation.
Figure 3:
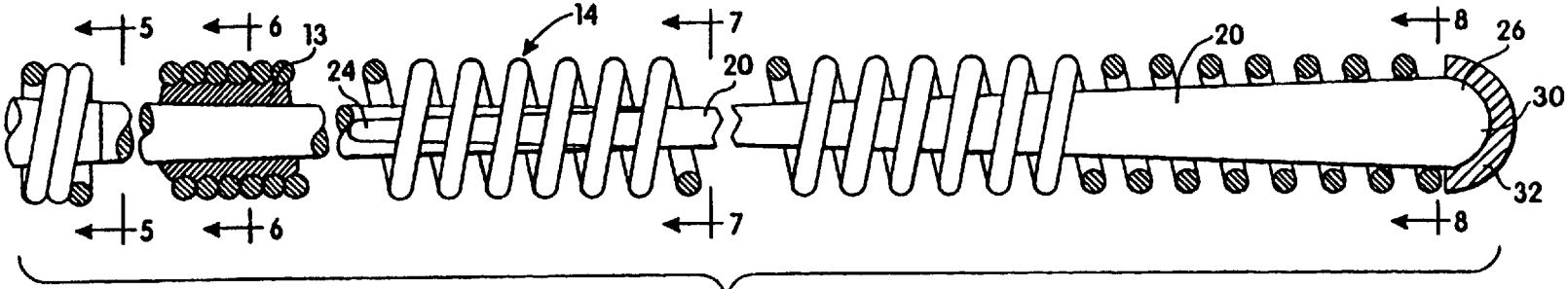
FIG. 3 is a further enlarged cross-sectional illustration of the tip portion of the guidewire as seen in plan, and illustrating the duck-bill configuration of the tip segment of the core wire in accordance with the invention.
Figure 8:
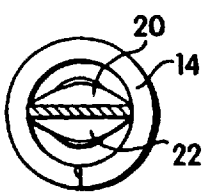
FIGS. 5–8 are cross-sectional illustrations of the guidewire as seen along the lines 5—5, 6—6, 7—7 and 8—8, respectively, of FIG. 3.
Figure 7:
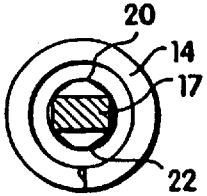
Figure 6:
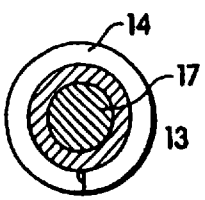
Figure 5:
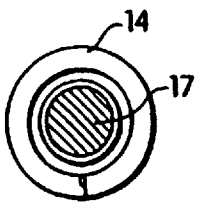

As shown in FIGS. 2–4, the distal portion of the shaft defines a core wire 17 that has a most distal segment 18 formed in a tapered configuration and further in which the tapered distal segment 18 is provided with flattened surfaces 20, 22. The flattened surfaces are formed so that they lie in planes at an angle to each other, thus defining a wedge-like configuration. Viewed in plan (FIG. 3), the flattened surfaces define somewhat of a "duck-bill" configuration in which the width of The flattened surface at the proximal end 24 is at a minimum, increasing in a distal direction to a maximum width at the distal end 26 of the flattened surface.

By way of one dimensional example, a guidewire incorporating the invention may have a coil 14 of the order of 30 cm long with the distal portion 12 of the shaft that defines the core wire 17 being of substantially the same length. In a guidewire having an outer diameter of the order of 0.012", the most distal segment 18 may extend from the next adjacent proximal segment which may be a cylindrical segment 28. For example, in a guidewire of 0.012" diameter, the most distal segment 18 may be of the order of 5 cm long. The more proximal cylindrical segment 28 may be of the order of 0.004" in diameter, with the most distal segment 18 being tapered to the more slender, duck-bill configuration. In this example, the flattened surfaces 20, 22 may extend over a length of approximately 4.0 cm and may have a thickness, at their proximal end 24 of the order of 0.001 inches and a width, at their distal end 26 of about 0.006 inches. The thickness (as seen in FIG. 4) at the most distal tip 26 of the segment 18 is of the order of 0.0007 to 0.0008 inches. The guidewire is constructed such that the distal tip 30 of the segment 18 is attached to and is incorporated into the hemispherical tip weld 32 at the distal tip of the coil.

As can be seen from FIGS. 5–8, the cross-sectional configuration of the core wire throughout the length of the flattened surfaces 20, 22 progressively changes, in a distal direction, from a configuration in which the flat occupies only a relatively small portion of the cross sectional circumference of the distal segment 18 to a progressively increasing portion and terminating, finally, in a thin, flat, relatively broad configuration. It is important to the practice of the invention that the transition from the circular cross-section of the distal segment 18 to the flattened cross-section is smooth and without any shoulders. Thus, the distal segment 18 presents a smooth transition from the round to the flattened segments that avoids stress risers that might tend to prolapse and kink.

Figure 9A:
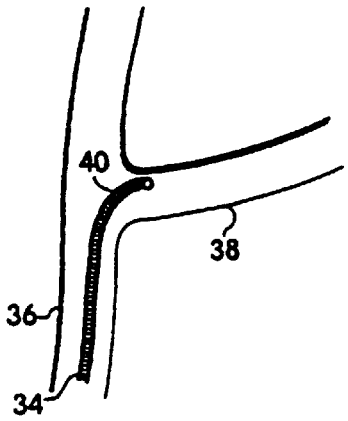
FIG. 9A is a diagrammatic illustration of a guidewire having a curved distal tip as the tip begins to enter a branch artery.
Figure 9B:
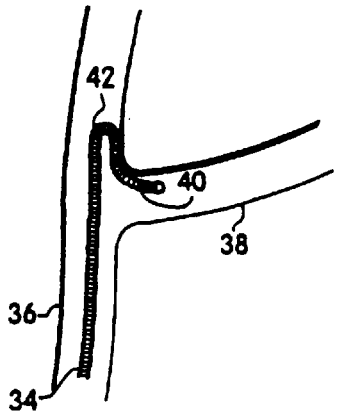
FIG. 9B is an illustration similar to 9A showing the manner in which the guidewire of FIG. 9A may prolapse upon continued advancement of the guidewire.
Figure 9C:
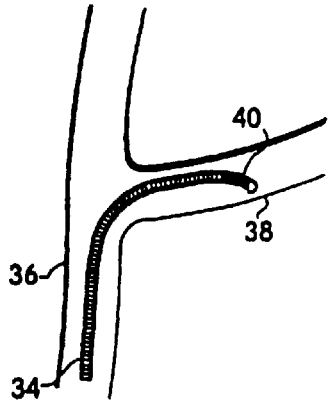
FIG. 9C is an illustration similar to FIG. 9A showing the manner in which the guidewire of the present invention avoids guidewire prolapse when entering branch arteries.

It has been found that a tip so constructed displays an improved combination of properties, including improved column strength and torsional rigidity at the tip while maintaining sufficient tip floppiness to conform to the contours of highly tortuous vascular anatomy. For example, FIGS. 9A, 9B and 9C illustrate the advantages of the improved column strength at the tip that is achieved with the invention. FIG. 9A illustrates a guidewire 34 that has been advanced through an artery 36 where it is desired to steer the guidewire into a branch artery 38. The distal tip of the guidewire 34 is curved, as indicated at 40, the curve being preset either during manufacture or by the physician by bending the tip to impart the bend to the shaping ribbon or distal tip of the core wire. Once the bent tip 40 is manipulated into the entry to the branch artery 38, the physician continues to advance the guidewire, by pushing and rotating the wire. Among the advantages of the invention is that by providing a tip structure that is free of shoulders and has improved column strength, the tip displays improved cornering ability, that is, the ability for the trailing portions of the guidewire to follow the leading portions of the guidewire. FIG. 9B illustrates the kind of difficulty that the present invention is intended to overcome. With prior guidewires although the bent tip 40 of the guidewire could be manipulated into the branch artery 38, continued advancement of the guidewire resulted in the more stiff, proximal portions sometimes continuing straight ahead rather than following the tip into the branch artery. This is illustrated in FIG. 9B, from which it may be seen that as the more stiff proximal trailing portion of the guidewire continues to advance past the entrance to the branch artery, the tip will bend sharply, as indicated at 42, and will prolapse. Continued advancement of the guidewire will drag the tip out of the branch artery. The bend 42 typically occurs at a stress riser where there is a sharp transition in the cross-sectional configuration of the core wire structure as in FIG. 11 or transition from ribbon to core as in FIG. 10. With the present invention, the improved column strength and absence of shard transitions increases substantially the tendency for the trailing portion of the guidewire to follow the leading distal tip.

Figure 10:
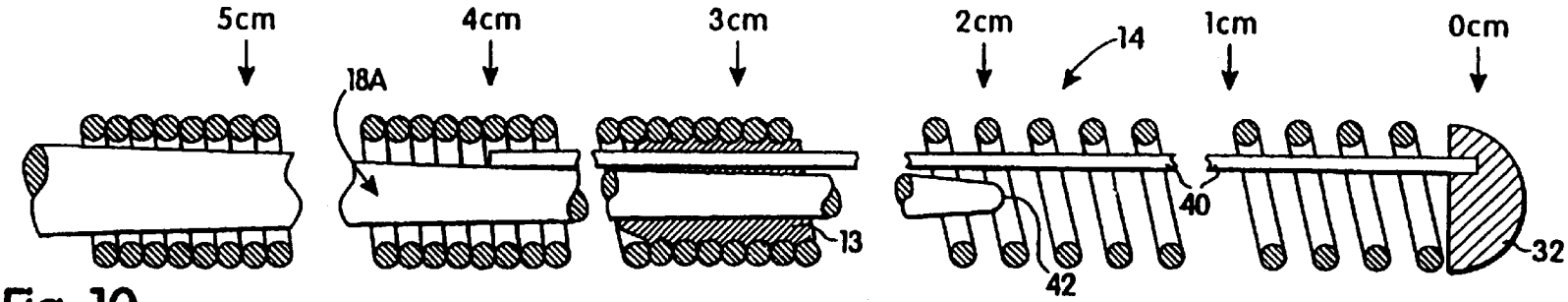
FIGS. 10, 11 and 12 are fragmented, sectional illustrations, respectively, of guidewire tip constructions in two prior art guidewires (FIGS. 10 and 11) as compared with the present invention (FIG. 12) with FIGS. 10, 11 and 12 being aligned with respect to each other and with respect to a dimensional scale indicating the distance between the various elements of the guidewire and the tip weld of the guidewire.
Figure 11:
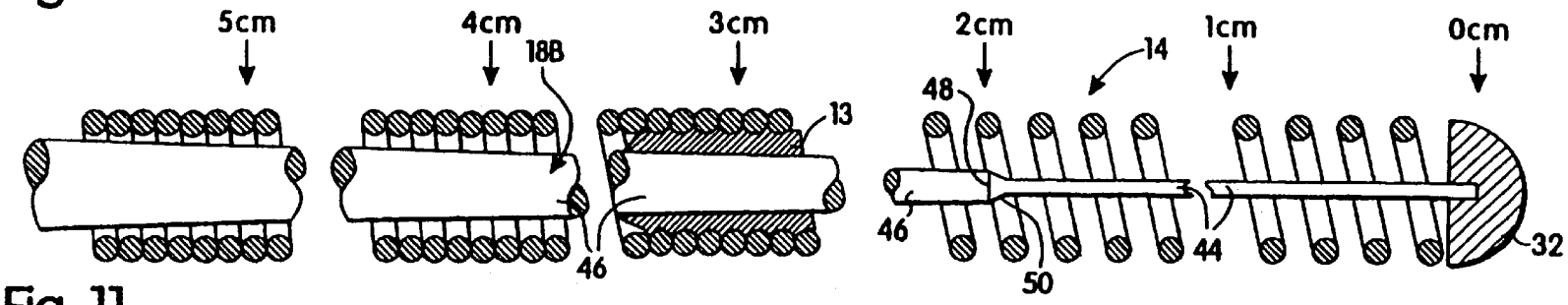
Figure 12:
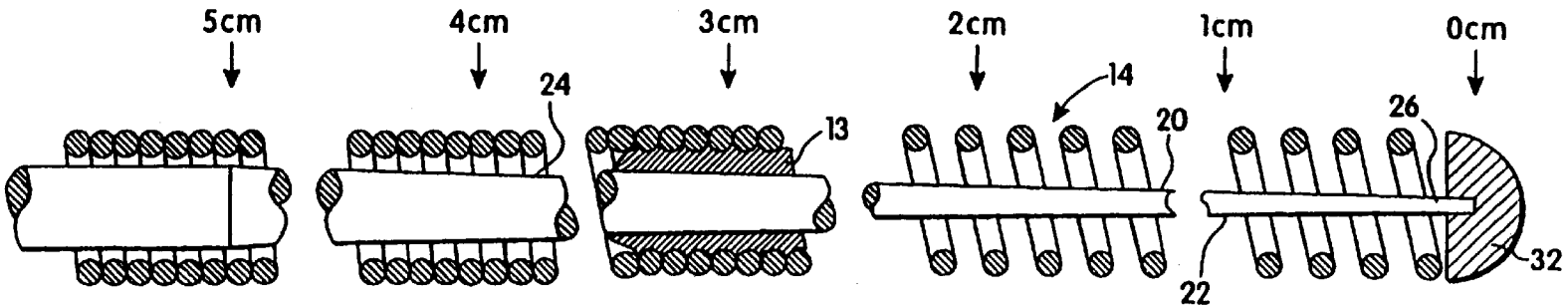

Another advantage of the invention is that it results in a tip construction having increased strength at the distal braze joint 13. The distal braze joint 13 serves as an additional connection between the core wire 17 and the helical coil 14 and, typically, is located 2 to 3 cm proximally from the distal tip of the coil 14. The advantages achieved in this aspect of the invention will be appreciated from FIGS. 10, 11 and 12 which illustrate in enlarged detail (out of scale for clarity of illustration), the comparative details of the tip construction of two prior art constructions with the present invention. FIGS. 10, 11 and 12 are aligned with respect to a scale for the purpose of illustrating the distances from the tip weld 32 of the guidewire of various elements of the guidewire, such as the distal braze joint, etc. FIG. 10 shows a conventional tip construction in which a distal tapered tip segment of the core wire 18A terminates short of the distal tip weld 32. A thin, flat shaping and safety ribbon 40 extends from the tip segment 18A to the tip weld 32. The shaping ribbon, which may be of rectangular cross-section, of the order of 0.001 inches thick by 0.003 inches wide and about 4 cm long is attached to the tip segment at the distal braze joint 13. The braze joint 13 also is attached securely to several turns of the helical coil 14. It will be appreciated that the shaping ribbon 40 overlaps the terminal distal portion of the tip segment 18A and extends distally beyond the tip 42 of the tip segment 18A. The distal tip of the ribbon 40 is incorporated into and attached to the tip weld 32. With the type of tip construction exemplified by FIG. 10, the region at the distal zip 42 of the core wire 18A presents a relatively sharp transition in stiffness and column strength. This type of guidewire construction displays a significant tendency to prolapse, as illustrated diagrammatically in FIG. 9B.

FIG. 11 illustrates another common type of guidewire tip construction in which a flat dropped segment 44 of the core wire 18B is used in place of the shaping ribbon 40 of FIG. 10. In the flat dropped construction exemplified in FIG. 11, the core wire 18B is formed with a cylindrical tip segment of uniform diameter which is hammered flat to a flat, ribbon-like configuration. Typically, the flat dropped tip segment 44 will be of substantially uniform cross sectional configuration along its length, being generally rectangular, of the order of 0.001 inches thick by 0.003 inches wide. The length of the flat dropped section 44 typically corresponds to the length of shaping ribbon 40 that extends beyond the distal tip 42 of the core wire 18A in FIG. 10. In the flat dropped embodiment of FIG. 11, the tip segment extends from the distal end of a tapered segment 46. As with the shaping ribbon embodiment of FIG. 10, the distal tip of the flat dropped segment 44 is attached securely to and is incorporated into the tip weld 32. In the embodiment of FIG. 11, the distal braze joint 13 is attached to the core wire 18B about 1 cm proximal of the juncture 48 of the tapered segment with the flat dropped distal segment. The construction typified by FIG. 11 results in a shoulder 50 at the juncture of the flat dropped segment 44 with the proximally adjacent portion that is not flattened. The shoulder 50 thus defines a relatively sharp transition in stiffness and column strength such that the type of guidewire exemplified by FIG. 11 also has a tendency to prolapse, as illustrated in FIG. 9B.

It should be understood that in the foregoing examples of prior art devices, the dimensions have been selected for purposes of comparative illustration with respect to the present invention (FIG. 12). It should be understood that variations in the dimensions may be incorporated for any specific guidewire. For example, it is common for manufacturers of such guidewires to provide shaping ribbons or flat dropped segments in varying lengths. The foregoing dimensional examples are considered to be typical.

FIG. 12 illustrates a guidewire constructed in accordance with the present invention. As described above, the core wire 17 includes a tapered tip segment 18 that is flattened over its distal approximately 4 cm to form the duck-bill configuration described. The phantom lines in FIG. 12 illustrate the configuration of the tapered tip segment 18 of the core wire before the flattening process (described below). The guidewire construction is characterized by its absence of sharp transitions or shoulders that might form stress risers. Additionally, the flattened surfaces 20, 22 are of progressively increasing width in a distal direction which provides for good torsional characteristics to enhance the steerability of the wire. The thickness of the core wire defined between the flattened surfaces 20, 22 thus decreases progressively from the proximal end of the flattened surfaces 20, 22 toward their distal end. As described in the foregoing dimensional example, the width at the distal end 26 of the flattened surfaces is of the order of 0.006 inches and is wider than the diameter of the tapered segment at the juncture of the tapered segment 18 with the proximal cylindrical segment 17. The relatively broad width of the tip 26 enhances the torsional responsiveness of the guidewire while maintaining sufficient softness in the tip to minimize trauma to the vessel.

It should be noted in a further aspect of the invention that may be incorporated into a wide variety of guidewires, the distal tip of the core wire is sufficiently broad to span the major portion of the inner diameter of the helical coil and, preferably, may span substantially the entire inner diameter of the helical coil at the distal end of the coil. Such an arrangement provides a relatively high aspect ratio (the ratio of the width to the thickness of the flat core wire). Preferably, the aspect ratio is at least 5 to 1 and may be higher.

In a guidewire constructed according to the embodiments disclosed in FIGS. 10 and 11, the diameter of the core wire 18, in the region of the distal braze joint 13 typically is of the order of 0.0025". In contrast, with the present invention, the geometry is such that the diameter of the core wire in the region of the distal braze is substantially greater and, for example, in the foregoing illustration, is of the order of 0.0032". Thus, for substantially equal core wire geometry, the structure at the distal braze joint is more massive for the present invention than with the prior art devices. For example, with a core wire that tapers from 0.004 inches (as exemplified by the embodiments of FIGS. 10 and 11), a compared to the present invention, as exemplified in FIG. 12 in which the tapered distal segment 18 tapers from 0.004 inches to 0.002 inches (before flattening,) the strength of the distal braze joint is substantially greater with the present invention. This presents a substantially increased diameter in that region and results in a significantly stronger joint which enhances the ability to transmit torque and rotation to the distal tip of the guidewire as well as the structural integrity and safety of the tip.

Figure 14:
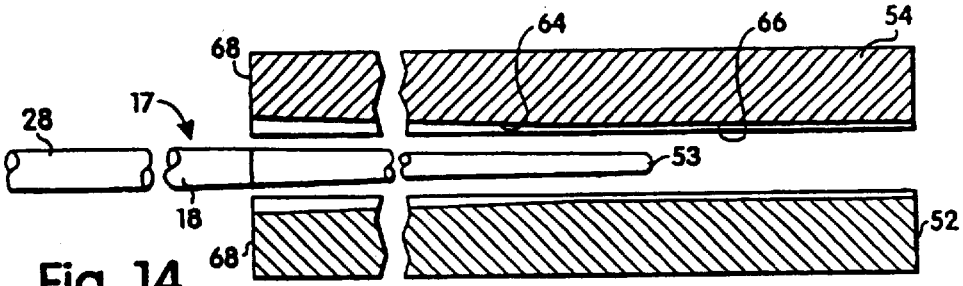
FIG. 14 is a diagrammatic illustration of the manner in which the dies of FIG. 13 receive a tapered tip portion of a core wire.

FIG. 14 illustrates the unflattened tapered tip before the flattening process in accordance with the invention. In the illustrative embodiment, the core wire may be formed to have a cylindrical segment 28 just proximally of the tapered tip segment 18. The cylindrical segment 28 typically may be of the order of 0.004" in diameter. The tapering tip segment 18 may be of the order of 5 cm long and, before flat dropping, may taper from about 0.004" to about 0.002" in diameter at its tip, indicated at 53. After flat dropping, as described below, the flat dropped surfaces 20, 22 may extend over a length of about 4.0 cm to define the duck-bill configuration described. By forming the flat dropped portion in a tapered (wedge-like) configuration, a progressive smooth, transition from the circular cross-section to the flattened configuration of the tapered tip segment is preserved.

Figure 13:
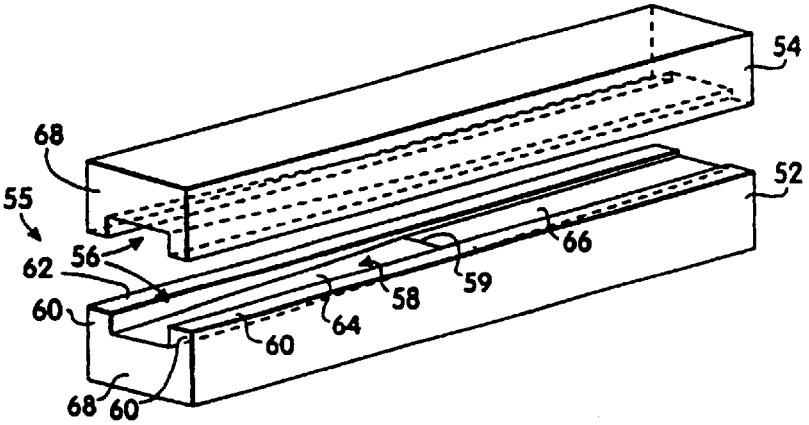
FIG. 13 is an illustration of a pair of dies that may be used in the manufacture of the tip of the present invention.
Figure 15:
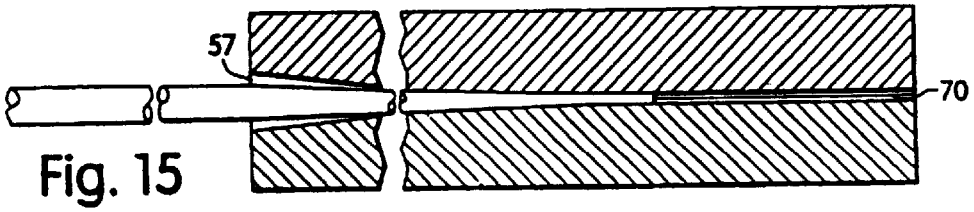
FIG. 15 is an illustration of the dies of FIG. 13, brought together under an impact load to form the flattened surfaces of the distal tip of the guidewire.

FIGS. 13–15 illustrate the dies that preferably may be used in order to effect the flattening of the distal tip as well as a tapered, unflattened tip in readiness to be flattened. As illustrated, the dies may include a pair of identical elongate dies 52 54, the die 52 serving as a stationary die with the die 54 being movable toward and away from the stationary die 52. Each die has a channel 56 extending lengthwise of the die, the channel 56 being defined by an elongate working surface 58 and a pair of side rails 60 that are substantially parallel to and extend above the level of the working surface 58. The rails 60 have facing surfaces 62 arranged so that the facing dies may be brought together with the facing surfaces 62 butting each other. The butting surfaces 62 define the limit to which the dies can be brought together. The working surfaces 58 of the dies are arranged so that when the dies are brought together and their butting surface are in engagement, the working surfaces 58 will define a configuration adapted to impress the wedge-like surfaces 20, 22 on the tapered distal tip segment 18 of the core wire 17.

By way of example, a pair of dies usable to make a guidewire in accordance with the invention and having the dimensions illustrated above, the dies may be of the order of 3 inches long. The working surface 58 may be considered as having a proximal portion 64 and a distal portion 66. The proximal portions 64 are inclined at the slight angle intended to be impressed on the core wire 17. The distal portions 66 are intended to be more closely parallel to the facing surfaces 62 of the side rails 60 so that when the dies are brought together, the distal portions will be oriented more parallel to each other than the angled proximal portions 64.

The height of the facing surfaces 62 on the rails 60 above the distal portion 66 of the working surface 58 preferably, in the illustrative embodiment, is of the order of 0.0004 inches. Thus, when the dies are brought together, and they will define a space 70 between facing distal portions 66 of the working surfaces 58 of about 0.0008". Preferably, the proximal portion 64 of the working surfaces may extend over a length of about 1.5 inches to 2.2 inches with 1.5 inches (3.81 cm) being preferred for the foregoing dimensional example. The working surface 58 and the butting surfaces 62 of the rail 60 preferablly are finished very smoothly, to about a number four microfinish.

When the stationary and movable dies 52, 54 are brought together, the space 57 between the surfaces 64 at the opening end 55 of the dies is greater than the maximum diameter of the unflattened tapered distal tip segment 18. In the illustrative embodiment, the height of the space at the opening may be of the order of 0.006", to receive a core wire having a tapered diameter at the juncture of the cylindrical segment 28 of about 0.004".

In making the guidewire of the foregoing dimensional example, the distal end of the guidewire is inserted to a length of about 5 cm from the proximal face 68 into the dies. The movable die 52 then is subjected to a sharp impact from a suitable device, such as a pneumatically driven hammer to forcibly bring the dies together thus deforming the tip segment 18 to the intended flattened, duck-bill configuration. Although about 5 cm length of the tapered core is inserted between the dies, it will be appreciated that only the distal 4.0 cm will actually be flattened because the spacing between the proximal working surfaces 64 at the proximal one centimeter of the dies in greater than the diameter of the core wire. It should be understood, however, that the dies described are illustrative only and that the dimensions for other dies to make other wires may be modified. It should be noted, however, that by forming the dies with respect to the tapered blank so that a length of the working surface at the proximal end of the dies will be spaced from the workpiece insures that the flattened surfaces 20, 22 will merge with the unflattened surface of the core wire in a shoulderless transition.

It should be noted that the region of transition from the proximal portions 64 of the working surface 58 to the distal portion 66 does not, in practice, define a clear, discernible line. Rather, The angle between the portions 64, 66 of the working surface 58 are so small (of the order of one-tenth of a degree) that to the naked eye, the entire working surface 58 appears smooth and flat. The phantom line 59 in FIG. 13 is only for purposes of illustration to suggest the transition from the proximal surface 64 to distal surface 66. Additionally, it should be noted that in the example described, when the distal tip segment 18 is inserted between the dies to a depth of 5 cm, about 1 cm of the length of the tip segment 18 will lie between and be deformed by the distal portion 66 of the working surface 58. Thus, in practice, a relatively short distal portion of the flattened surfaces 20, 22 may be more parallel. In practice, however, the surfaces 20, 22 appear to present a smooth continually tapering surface notwithstanding the possibly more parallel configuration of the distal portions 66 of the working surfaces 58. It should be understood, however, that it is difficult to measure precisely the angles of such surface and, as a practical matter, it is not critical whether the distal half centimeter or so of the surfaces 20, 22 are precise continuations of the taper or whether they are slightly more parallel. Other dies could be used which are more "theoretically" perfect although it is not felt this would substantially change the tip characteristics. In either case, the surfaces 20, 22 present a progressive taper, without sharp shoulders or transitions and with a progressive widening to the duck-bill configuration as described.

From the foregoing, it will be appreciated that the invention provides a guidewire having a tip construction that provides a number of advantages over the prior art. The guidewire displays improved column strength in its tip region so as to present improved cornering ability, that is, a greater tendency for the more proximal portions of the guidewire to follow the distal tip from one artery into an angled branch artery. Moreover, the improved resistance to prolapse is achieved in a guidewire having good torsional characteristics to facilitate steering of the device as well as sufficient floppiness to enable the wire to conform to tortuous anatomy such as may be encountered in PTCA. Additionally, the invention results in the use of a guidewire tip having a more massive structure at the distal braze joint for substantially equal core wire geometry further to facilitate the steerability of the guidewire.

It should be understood, however, that the foregoing description of the invention is intended merely to be illustrative thereof and that other embodiments, modifications and equivalents thereof may be apparent to those skilled in the art without departing from its spirit. For example only, the invention has been described with reference to specific dimensional examples and in the context of the guidewire adapted particularly for use in PTCA procedures. It should be understood, however, that the invention may be practised with variously dimensioned guidewires. Although the invention is suited particularly for use in angioplasty and specifically coronary angioplasty, it may be adapted for guidewires used in other procedures as well.

Having thus described the invention what I desire to claim and secure by Letters Patent is:

1. In a guidewire adapted for use with a catheter, the guidewire including a helical coil at its distal end and a core wire having a longitudinal axis and extending through the helical coil, the improvement comprising:

the core wire having a distal tip portion that is tapered and includes a pair of opposed flattened surfaces along the tapered portion, the flattened surfaces extending distally at an angle outward to the longitudinal axis of the core wire, the juncture of the flattened and unflattened surfaces being free of sharp cross-sectional transitions.

2. In a guidewire as defined in claim 1, the improvement further comprising:

tip portion being substantially shoulderless.

3. In a guidewire as defined in claim 1, the improvement further comprising the flattened surfaces each having a proximal end and a distal end, the proximal ends of the flattened surfaces being narrower in width than the distal ends.

4. In a guidewire as defined in claim 3, the improvement further comprising:

the width of the flattened surfaces increasing progressively from the proximal to the distal ends of said surfaces.

5. In a guidewire as defined in claim 3, the improvement further comprising:

the width of the flattened surfaces at the distal end of the distal tip portion being greater than the diameter of the distal tip portion immediately adjacent the proximal end of the flattened surfaces.

6. In a guidewire as defined in claim 5, the improvement further comprising:

the width of the flattened surface at the tip of the helical coil occupying the major portion of the inner diameter of the helical coil.

7. In a guidewire as defined in claim 6, the improvement further comprising:

the width of the flattened surface occupying substantially the full inner diameter of the coil at the tip of the coil.

8. In a guidewire as defined in claim 5, the improvement further comprising:

the ratio of the width to the thickness of the flattened surfaces, at their distal ends, being not less than about 5 to 1.

9. In a guidewire as defined in claim 5, the improvement further comprising:

the ratio of the width to the thickness of the flattened surfaces, at their distal ends, being not less than about 7 to 1.

10. In a guidewire as defined in claim 1, the improvement further comprising:

the coil being attached securely to the distal tip portion of the core wire at a location that intersects the flattened surfaces.

11. In a guidewire as defined in claim 10, the improvement further comprising:

the attachment being defined at a distal braze joint.

12. In a guidewire as defined in any one of claims 1–11 wherein said guidewire comprises an angioplasty guidewire.

13. A guidewire for use with a catheter comprising:

an elongate flexible shaft having a proximal end and a distal end;

a helical coil mounted about the distal portion of the shaft, the portion of the shaft extending through the helical coil defining a core wire;

the helical coil being attached to the shaft at the proximal end of the helical coil;

the core wire having a distal tip portion that is tapered and includes a pair of opposed flattened surfaces along the tapered portion, the flattened surfaces extending distally at an angle outward to the longitudinal axis of the core wire, the juncture of the flattened and unflattened surfaces being free of sharp cross-sectional transitions.

14. In a guidewire as defined in claim 13, the improvement further comprising:

tip portion being substantially shoulderless.

15. In a guidewire as defined in claim 13, the improvement further comprising the flattened surfaces each having a proximal end and a distal end, the proximal ends of the flattened surfaces being narrower in width than the distal ends.

16. In a guidewire as defined in claim 15, the improvement further comprising:

the width of the flattened surfaces increasing progressively from the proximal to the distal ends of said surfaces.

17. In a guidewire as defined in claim 15, the improvement further comprising:

the width of the flattened surfaces at the distal end of the distal tip portion being greater than the diameter of the distal tip portion immediately adjacent the proximal end of the flattened surfaces.

18. In a guidewire as defined in claim 17, the improvement further comprising:

the width of the flattened surface at the tip of the helical coil occupying the major portion of the inner diameter of the helical coil.

19. In a guidewire as defined in claim 18, The improvement further comprising:

the width of the flattened surface occupying substantially the full inner diameter of the coil at the tip of the coil.

20. In a guidewire as defined in claim 17, the improvement further comprising:

the ratio of the width to the thickness of the flattened surfaces, at their distal ends, being not less than about 5 to 1.

21. In a guidewire as defined in claim 17, the improvement further comprising:

the ratio of the width to the thickness of the flattened surfaces, at their distal ends, being not less than about 7 to 1.

22. In a guidewire as defined in claim 14, the improvement further comprising:

the coil being attached securely to the distal tip portion of the core wire at a location that intersects the flattened surfaces.

23. In a guidewire as defined in claim 22, the improvement further comprising:

the attachment being defined at a distal braze joint.

24. In a guidewire as defined in any one of claims 13—23 wherein said guidewire comprises an angioplasty guidewire.

[25. In a guidewire adapted for use with a catheter, the guidewire including a helical coil at the distal end of the guidewire and a core wire extending through the helical coil to the distal tip, the improvement comprising:

the distal portion of the core wire being substantially flat and having a width that spans the major portion of the inner diameter of the helical coil.]

[26. In a guidewire as defined in claim 1, the improvement further comprising:

the flat tip of the core wire spans substantially the entire inner diameter of the helical coil at the distal tip of the helical coil.]

27. In a method for forming a medical guidewire, the improvement comprising:

providing a core wire having a tapered distal tip portion;

impressing a pair of opposed flattened surfaces along the tapered portion, the flattened surfaces extending distally at an angle outward to the longitudinal axis of the core wire, the juncture of the flattened and unflattened surfaces being free of cross-sectional transitions.

28. The method of claim 27, comprising inserting the distal tip of the core wire between a pair of dies, bringing the dies together and impressing wedge-like surfaces on the distal tip portion of the core wire.

29. The method of claim 28, wherein one of the dies is stationary and the second die is moveable toward and away from the stationary die.

30. The method of claim 28, wherein each die has a channel extending lengthwise of the die and the channels define an elongate working surface and each die having a butting surface which defines the limit to which the dies can be brought together.

31. The method of claim 30, wherein the elongate working surfaces of the dies have a proximal portion inclined at an angle sought to be impressed on the distal end of the core wire and have distal portions which are more closely parallel to the butting surfaces of the dies.

32. The method of claim 30, wherein the working surfaces are, finished smoothly.

33. The method of claim 31, wherein a space between surfaces of the proximal portions of the dies at an opening end of the dies is greater than a maximum diameter of an unflattened tapered distal tip segment of the core wire.

34. The method of claim 29, comprising subjecting the moveable die to a sharp impact to forcibly bring the dies together and thus deforming the distal tip portion of the core wire.

35. The method of claim 30, wherein the dies are formed such that a length of the working surface at the proximal end of the dies is spaced from the core wire such that flattened surfaces of the core wire will merge with an unflattened surface of the core wire in a shoulderless transition.

*36. In a guidewire adapted for use with a catheter, the guidewire having a proximal end and a distal end, wherein the distal end has a distal tip, the guidewire including a helical coil at the distal end of the guidewire and a core wire extending through the helical coil to the distal tip of the guidewire, the improvement comprising:*

*the core wire having a distal segment with a pair of opposed surfaces that are substantially flat and a distal tip, wherein the thickness of the distal segment of the core wire is progressively tapered toward the distal tip of the core wire without sharp shoulders or cross-sectional transitions.*

*37. In a guidewire adapted for use with a catheter, the guidewire having a proximal end and a distal end, wherein the distal end has a distal tip, the guidewire including a helical coil at the distal end of the guidewire and a core wire extending through the helical coil to the distal tip of the guidewire, the improvement comprising:*

*the core wire having a distal segment with a pair of opposed surfaces that are substantially parallel and a distal tip, wherein the thickness of the distal segment of the core wire is progressively tapered toward the distal tip of the core wire without sharp shoulders or cross-sectional transitions.*

*38. In a guidewire adapted for use with a catheter, the guidewire having a proximal end and a distal end, wherein the distal end has a distal tip, the guidewire including a helical coil at the distal end of the guidewire and a core wire extending through the helical coil to the distal tip of the guidewire, the improvement comprising:*

*the core wire having a distal segment with a pair of opposed surfaces that are substantially flat and a distal tip, wherein the thickness of the distal segment of the core wire is progressively tapered toward the distal tip of the core wire without sharp shoulders or cross-sectional transitions and the width of the distal segment of the core wire progressively widens in cross-section to the distal tip of the core wire.*

*39. In a guidewire adapted for use with a catheter, the guidewire having a proximal end and a distal end, wherein the distal end has a distal tip, the guidewire including a helical coil at the distal end of the guidewire and a core wire extending through the helical coil to the distal tip of the guidewire, the improvement comprising:*

*the core wire having a distal segment with a pair of opposed surfaces that are substantially flat and a distal tip, wherein the thickness of the distal segment of the core wire is progressively tapering to the distal tip of the core wire without sharp shoulders or cross-sectional transitions.*

*40. In a guidewire as defined in claim 1, the improvement further comprising:*

*the flat tip of the core wire spans substantially the entire inner diameter of the helical coil at the distal tip of the helical coil.*

* * * * *